United States Patent
Legay et al.

(10) Patent No.: US 12,083,351 B2
(45) Date of Patent: Sep. 10, 2024

(54) SUBCUTANEOUS IMPLANTABLE MEDICAL DEVICE AND A METHOD OF PROCESSING SIGNALS OF A SUBCUTANEOUS IMPLANTABLE MEDICAL DEVICE

(71) Applicant: SORIN CRM SAS, Clamart (FR)

(72) Inventors: Thierry Legay, Fontenay les Brits (FR); Rafael Cordero Alvarez, Paris (FR); Delphine Feuerstein, Boulogne Billancourt (FR)

(73) Assignee: SORIN CRM SAS, Clamart (FR)

( * ) Notice: Subject to any disclaimer, the term of this patent is extended or adjusted under 35 U.S.C. 154(b) by 786 days.

(21) Appl. No.: 16/920,103

(22) Filed: Jul. 2, 2020

(65) Prior Publication Data
US 2021/0001136 A1    Jan. 7, 2021

(30) Foreign Application Priority Data
Jul. 5, 2019 (FR) ...................................... 1907534

(51) Int. Cl.
*A61N 1/39* (2006.01)
(52) U.S. Cl.
CPC ......... *A61N 1/3956* (2013.01); *A61N 1/3943* (2013.01); *A61N 1/3968* (2013.01)
(58) Field of Classification Search
CPC ... A61N 1/3956; A61N 1/3943; A61N 1/3968
(Continued)

(56) References Cited

U.S. PATENT DOCUMENTS 5,456,706 A   10/1995  Pless et al.
8,577,455 B2  11/2013  Mitrani et al.
(Continued)

FOREIGN PATENT DOCUMENTS

DE   19800697 A1   7/1999
EP   2 368 493 A1  9/2011
(Continued)

OTHER PUBLICATIONS

European office action on EP application No. 20183499.1 dated Dec. 1, 2020. 14 pages.
(Continued)

*Primary Examiner* — Allen Porter
*Assistant Examiner* — Daniel Tehrani

(57) ABSTRACT

A subcutaneous implantable active medical device, in particular a subcutaneous cardiac defibrillator, comprising a housing and a subcutaneous implantable lead connected to the housing. The subcutaneous implantable lead comprises a plurality of sensing electrodes forming at least two dipoles from which at least two electrical signals are collected concurrently. The first dipole having a first length less than a second length of the second dipole. The subcutaneous implantable active medical device further comprises a controller configured to determine whether or not tachyarrhythmia is present by determining a criterion of similarity based on the electrical signals collected concurrently via the first dipole and via the second dipole during a defined series of cardiac cycles that is such that detection of a depolarization peak, corresponding to detection of an R wave, is performed via the first dipole.

15 Claims, 7 Drawing Sheets

(58) Field of Classification Search
USPC .............................................................. 607/5
See application file for complete search history.

(56) References Cited

U.S. PATENT DOCUMENTS

| | | | |
|---|---|---|---|
| 10,987,517 B2 * | 4/2021 | Cheng .................... | A61B 5/349 |
| 2005/0049644 A1 | 3/2005 | Warren et al. | |
| 2010/0249626 A1 * | 9/2010 | El Arab ................. | A61B 5/363 |
| | | | 600/518 |
| 2011/0118804 A1 * | 5/2011 | Henry .................... | A61B 5/024 |
| | | | 600/407 |
| 2014/0330325 A1 * | 11/2014 | Thompson-Nauman | ................... |
| | | | A61N 1/365 |
| | | | 607/15 |
| 2015/0112414 A1 | 4/2015 | Conger et al. | |
| 2015/0306410 A1 | 10/2015 | Marshall et al. | |
| 2016/0287876 A1 | 10/2016 | Euzen et al. | |
| 2017/0312494 A1 | 11/2017 | Seifert et al. | |
| 2019/0054290 A1 * | 2/2019 | De Kock ............... | A61N 1/057 |
| 2019/0111265 A1 | 4/2019 | Zhou | |
| 2019/0117990 A1 * | 4/2019 | Euzen .................... | A61N 1/025 |
| 2019/0298991 A1 | 10/2019 | Bomzin et al. | |

FOREIGN PATENT DOCUMENTS

| | | |
|---|---|---|
| EP | 2 742 971 A1 | 6/2014 |
| JP | 2006-508774 A | 3/2006 |
| JP | 2006518631 A | 8/2006 |
| JP | 2006-522650 A | 10/2006 |
| JP | 2007-500549 A | 1/2007 |
| JP | 2008-526462 A | 7/2008 |
| WO | 9217240 A1 | 10/1992 |
| WO | 2017192870 A1 | 11/2017 |

OTHER PUBLICATIONS

Office Action issued in Japanese application No. 2020-115480 dated Sep. 29, 2021. 12 Pages.
Search Report for FR Application No. 1907534 dated Feb. 24, 2020. 12 pages.
European Patent Office, Application No. 20183494.2, Office Action dated Nov. 11, 2020, 8 pages.
European Patent Office, Application No. 2018499.1, Office Action, dated Dec. 1, 2020, 14 pages.
French Patent Office, Application No. 1907532, Office Action dated Mar. 10, 2020, 8 pages.
French Patent Office, Application No. 1907534, Search Report, dated Feb. 28, 2020, 12 pages.
Japanese Patent Office, Application No. 2020-115478, Office Action dated Aug. 13, 2021, 10 pages.
Japanese Patent Office, Application No. 2020-115480, Office Action, dated Sep. 29, 2021, 12 pages.

* cited by examiner

SUBCUTANEOUS IMPLANTABLE MEDICAL DEVICE AND A METHOD OF PROCESSING SIGNALS OF A SUBCUTANEOUS IMPLANTABLE MEDICAL DEVICE

CROSS-REFERENCE TO RELATED PATENT APPLICATIONS

This application claims the benefit of and priority to French Application No. 1907534, filed Jul. 5, 2019, which is incorporated herein by reference in its entirety.

BACKGROUND

The present invention relates to a method of processing signals for a subcutaneous implantable cardiac device, and to such a subcutaneous implantable cardiac device, in particular a subcutaneous implantable defibrillator.

A conventional, i.e. transvenous-type, implantable automatic defibrillator, also known as an "Implantable Cardioverter-Defibrillator" or "ICD", comprises a defibrillation pulse generator and a microprocessor monitoring and control unit that are housed in a metal housing that is generally implanted in the pectoral pouch. That housing is connected to one or more leads that are inserted into the subclavian vein until they reach the heart. Inside the heart, the distal ends of the leads are attached to the inside walls of the cardiac cavities, where they can record electrograms (EGMs) that reflect the electrophysiological functioning of the heart. On the basis of the EGMs, treatment in the form of defibrillation (defibrillation shock) is administered (or interrupted) in order to terminate ventricular tachyarrhythmia that is life-threatening, such as ventricular tachycardia and ventricular fibrillation.

The weakest elements of such transvenous implantable automatic defibrillators (and of cardiac stimulators or "pacemakers" and similar devices) are the intracardiac leads. Indeed, lead breakage is one of the most common causes of malfunctioning of pacemakers. Extracting an implanted ICD lead (or an implanted pacemaker lead) is a procedure suffering from high morbidity and high mortality, and is generally performed only in the event of serious systemic infection that cannot be treated using antibiotics. In the majority of situations, broken leads are disconnected from the device and left in the heart. A new lead is then implanted next to the old one, and is connected to the implantable automatic defibrillator. However, that solution is possible only when sufficient space remains in the vein, because the presence of more leads can give rise to a venous occlusion. Therefore, using intracardiac leads is not ideal for young patients, who might need a multitude of leads during their lives.

A solution to the above-mentioned problems associated with intracardiac leads consists in replacing them with subcutaneous leads. In that way, in the absence of contact with heart or with the blood, the risk of systemic infection is eliminated and the veins are no longer obstructed. Furthermore, unlike extracting intracardiac leads, extracting subcutaneous leads is less traumatic and does not have any risk of mortality, because subcutaneous leads do not touch the heart. As a result, the leads can be removed very safely in the event they break, and can then be replaced with new subcutaneous leads, without any risk for the patient.

The main challenges with subcutaneous implantable devices are related to the reduction in the signal-to-noise ratio of the signals recorded subcutaneously and to the increase in the energy required for a successful defibrillation. Rather than recording EGMs, subcutaneous implantable devices record sub-cutaneous electrocardiograms (ECGs), which capture electrophysiological activity that is spatially averaged in the far field. The P waves and the T waves are then larger in the subcutaneous signals relative to the R waves, making it more difficult to detect the R-R interval, on which numerous tachyarrhythmia detection algorithms are based. Non-cardiac noise sources, such as myopotentials, can also degrade the subcutaneous signals and interfere with the detection algorithms, thereby disrupting the processing and the treatment. In addition, subcutaneous signals tend to be more sensitive to changes in posture than intracardiac signals are. Overall, those difficulties result in a detection procedure that is more complex than with conventional implantable automatic defibrillators. Algorithms or methods for processing endocardial electrogram signals, as known from EP 2 105 843 A1 and from EP 2 368 493 A1, are configured to make it possible to discriminate between genuine ventricular tachycardia (VT) and supraventricular tachycardia (SVT). However, those known algorithms are not adapted to detecting tachyarrhythmia on the basis of signals collected subcutaneously. Indeed, since subcutaneous defibrillators are more liable to suffer from over-detection or "oversensing" of noise and of P waves or T waves, it is necessary, in the particular situation of subcutaneous defibrillators, to minimize the risk of diagnosing VT or ventricular fibrillation (VF) when noise or P waves or T waves are oversensed. For example, in an implantable automatic defibrillator, erroneous interpretation of the collected signals could result in an inappropriate shock that could be traumatic or even harmful for the patient.

SUMMARY

In view of the above-mentioned limitations, there is a need to improve the processing of signals collected via a subcutaneous lead, in particular so as to be able to confirm whether or not tachyarrhythmia is present and so as to be able to distinguish oversensing of T or P waves (or of noise) from tachyarrhythmia.

An object of the present invention is thus to improve the processing of signals collected by means of a subcutaneous lead of a subcutaneous medical device, in particular to improve the sensitivity and the specificity of the detection or "sensing" and of the discrimination of the tachyarrhythmia episodes recorded using a subcutaneous lead.

The present invention achieves this object by providing a subcutaneous implantable active medical device, in particular a subcutaneous cardiac defibrillator, comprising: a housing; and a subcutaneous implantable lead connected to the housing; the subcutaneous implantable lead comprising a plurality of sensing electrodes forming at least two dipoles from which at least two electrical signals are collected concurrently; the first dipole having a length less than the length of the second dipole; the device further comprising a controller configured to determine whether or not tachyarrhythmia is present by determining a criterion of similarity based on the electrical signals collected concurrently via the first dipole and via the second dipole during a defined series of cardiac cycles that is such that detection of a depolarization peak, corresponding to detection of an R wave, is performed via the first dipole.

Detecting a depolarization peak on the basis of the signals collected via the first dipole makes it possible to improve the quality of subcutaneous detection of the R wave because the first dipole is the shorter of the two dipoles of the subcutaneous lead, and is thus less exposed to the risk of oversensing of noise or to the risk of error when detecting the QRS complex than the second dipole is. Indeed, the distance covered between the electrodes of the first dipole is short, thereby reducing the risks of the signals being degraded by an external source. For example, there is less muscle mass between the electrodes that can introduce myopotentials.

In providing a subcutaneous implantable active medical device, the present invention may be further improved by means of the following embodiments.

In one embodiment of the invention, the signals collected via the first dipole and via the second dipole of the subcutaneous implantable lead may be considered over a time window comprising a QRS complex and centered on detection of the R wave; the detection of the R wave being performed via the first dipole only.

Thus, the R-R interval of the signals collected via the first dipole can be determined and a time window, e.g. a time window of in the range 80 milliseconds (ms) to 150 ms, and in particular a time window of 100 ms, can be centered on the detection of the R wave that is performed via the first dipole. Detection of the R wave is thus not performed on the second dipole so as not to add any further computing cost. The signals from the second dipole that are collected concurrently with the signals from the first dipole, in particular during a time window only, can be recorded in a memory of the device.

In one embodiment of the invention, the controller may be configured to combine the signals collected via the first dipole and the signals collected via the second dipole, and, on the basis of the representation of the signals collected via the second dipole as a function of the signals collected via the first dipole, to determine a two-dimensional curve that is parameterized as a function of time and that is representative of the cardiac activity of a patient, the criterion of similarity being defined by comparison, in particular by a correlation, between said two-dimensional curve and a reference two-dimensional curve that is representative in a normal sinus rhythm.

Having the two-dimensional curve determined by the controller makes it possible to combine signals collected via the first dipole with signals collected via the second dipole: it is thus made possible for the information coming from the two dipoles of the subcutaneous lead to be taken into account simultaneously, in particular by considering—depending on the dipole—different electrical signal morphologies, thereby contributing to obtaining parameters relating to the origin of the collected signal that are more relevant. Such parameters relating to the origin of the collected signal participate, in particular, in determining the criterion of similarity.

In one embodiment of the invention, the controller may be further configured to identify presence or absence of undesirable noise in the collected signals as a function of the change of sign of at least one of the coordinates of a tangent vector between each pair of successive points of a plurality of points of said two-dimensional curve. More precisely, the controller may be configured to identify presence of undesirable noise by determining the number of times at least one of the coordinates of the tangent vector changes sign between each pair of successive points of the plurality of points of said two-dimensional curve and by comparing that number with a predetermined threshold number indicative of undesirable noise.

Indeed, for a non-noisy cardiac cycle, a relationship or ratio exists between the signals detected on the two dipoles that means that the two-dimensional curve is represented in essentially uniform manner. Conversely, for a noisy cardiac cycle, i.e. for a cycle comprising artifacts of extracardiac origin, the two-dimensional curve can be represented erratically. Such an erratic representation may be characterized by the number of times that at least one of the coordinates of the tangent vector changes sign between each pair of successive points of the two-dimensional curve. The controller is thus adapted to identify presence of noise in the collected signals by means of computing that is fast and cost effective in terms of software resources. The controller of the device could be configured to go over to a "noise mode" for a certain lapse of time, e.g. for 30 seconds, by increasing the threshold for detection of the R waves or by lengthening the refractory periods.

In one embodiment of the invention, the controller may be further configured to determine presence or absence of tachyarrhythmia by determining a criterion of majority that is determined on the basis of the criterion of similarity by computing the number of cycles that are similar between the collected signals and reference signals that are representative of a normal sinus cycle.

Thus, using the criterion of majority, confirmation of presence of a tachyarrhythmia episode can be deduced. Conversely, it might concluded that oversensing of the T wave and/or of the P wave has taken place, and that therefore no particular treatment is required. The device is thus configured to be able to distinguish oversensing of T or P waves (or of noise) from tachyarrhythmia; which is necessary in the particular situation of subcutaneous defibrillators, which are more liable to oversense noise and/or P or T waves than transvenous defibrillators are.

In one embodiment of the invention, the subcutaneous implantable lead may further comprise a defibrillation electrode. In addition, the controller may be configured to trigger a defibrillation operation by means of the defibrillation electrode when the criterion of similarity indicates the presence of tachyarrhythmia to be treated.

Thus, the subcutaneous implantable medical device is adapted not only to detect a tachyarrhythmia episode but also to treat such a condition, if necessary by delivering defibrillation electrical pulses.

In one embodiment of the invention, the subcutaneous implantable active medical device further comprises an accelerometer and/or a gyroscope in such a manner that the controller is configured to determine the position of the patient by means of the accelerometer and/or of the gyroscope;
the controller further being configured to determine the criterion of similarity by comparing said two-dimensional curve with a reference two-dimensional curve in said determined position, which reference two-dimensional curve is representative in a normal sinus rhythm.

Subcutaneous signals are more sensitive to posture than endocardial signals are. Thus, by making it possible to detect the position of the patient, interpretation of the collected electrical signals can be made finer, and therefore improved.

The object of the present invention is also achieved by providing a method of processing electrical signals collected concurrently on a first dipole and on a second dipole, which dipoles are formed by electrodes of a subcutaneous implantable lead of a subcutaneous implantable medical device, in the time domain during a defined series of cardiac cycles, the method comprising the steps of: 1) determining a two-dimensional curve parameterized as a function of time and representative of the cardiac activity of a patient by plotting the signals collected via the second dipole as a function of the signals collected via the first dipole, and determining a tangent vector at a plurality of points of said two-dimensional curve; and 2) identifying presence or absence of undesirable noise in the collected signals as a function of the change of sign of at least one of the coordinates of the tangent vector between each pair of successive points of the plurality of points of said two-dimensional curve; and/or 3) confirming presence or absence of a tachyarrhythmia episode on the basis of a criterion of similarity between said two-dimensional curve and a reference two-dimensional curve that is representative of a normal sinus rhythm.

Step 1) of determining the two-dimensional curve makes it possible to combine signals collected using a first dipole with signals collected using a second dipole: it is thus made possible to take into account simultaneously information coming from two dipoles of a subcutaneous lead, in particular by considering—depending on the dipole—different electrical signal morphologies, thereby contributing to obtaining parameters relating to the origin of the collected signal that are more relevant. In addition, since signals collected subcutaneously are particularly exposed to undesirable noise, step 2) of the method makes it possible to identify presence or absence of undesirable noise, and to do so by means of the same two-dimensional curve, thereby making it possible to reduce the computing costs in terms of software resources, because the noisy cycles are not processed or taken into consideration during processing of the collected signals. Finally, step 3) of the method makes it possible to discriminate between presence or absence of tachyarrhythmia, this discrimination also be effected on the basis of said two-dimensional curve. The method of the present invention for processing signals is thus specifically adapted and optimized for a subcutaneous implantable medical device.

In providing a method of processing electrical signals, the present invention may be further improved by means of the following embodiments.

In one embodiment of the invention, step 1) of the method may be preceded by an initial analysis step, in particular an analysis of the heart rhythm and/or of the heat rate, in order to detect potential presence of a tachyarrhythmia episode in the collected signals, and, in the initial analysis step, the signals collected via one of the dipoles of the subcutaneous implantable lead are compared with a predetermined tachyarrhythmia threshold.

In particular, this initial comparison step is implemented for the signals from the dipole and comprises detecting the QRS complex, in particular detecting the R wave. This initial comparison step thus comprises comparing the R-R interval with the predetermined tachyarrhythmia threshold. Since this step requires the R wave to be detected on one of the two dipoles only, the computing costs of the method of the present invention can be minimized.

In one embodiment of the invention, step 1), step 2) and/or step 3) may be performed only if potential presence of a tachyarrhythmia episode in the collected signals is detected in the initial analysis step.

Thus, steps 1, 2) and 3) of the method of processing the signals are not performed systematically but rather only if the presence of a tachyarrhythmia episode is suspected. This makes it possible to further reduce the computing costs of the method, by avoiding unnecessary computing steps.

In one embodiment of the invention, in step 2), presence of undesirable noise may be identified if the number of times at least one of the coordinates of the tangent vector changes sign between each pair of successive points of the plurality of points of said two-dimensional curve is greater than a predetermined threshold number indicative of undesirable noise.

Indeed, for a non-noisy cardiac cycle, a relationship or ratio exists between the signals detected on the two dipoles that means that the two-dimensional curve is represented in essentially uniform manner. Conversely, for a noisy cardiac cycle, i.e. for a cycle comprising artifacts of extracardiac origin, the two-dimensional curve can be represented erratically. Such an erratic representation may be characterized by the number of times that at least one of the coordinates of the tangent vector changes sign between each pair of successive points of the two-dimensional curve. Step 2) of the method thus provides a computing step that is fast and cost effective for identifying undesirable noise in the signals.

In one embodiment of the invention, the predetermined threshold number indicative of undesirable noise may be defined relative to all of the plurality of points of said two-dimensional curve.

Thus, identification of undesirable noise may be determined exhaustively by considering all of the points of the plurality of points of the two-dimensional curve, i.e. by taking into account the information contained at each point of the curve.

In one embodiment of the invention, step 3) is performed on the basis of signals in which potential presence of a tachyarrhythmia episode has been detected in the initial analysis step, and in which undesirable noise has not been identified in step 2).

In order to mitigate the limitations specifically related to signals collected subcutaneously, such as oversensing of noise, the method guarantees that the step for confirming presence or absence of a tachyarrhythmia episode is triggered only for signals of a cycle considered as being valid in step 2), i.e. for signals of a non-noisy cycle.

In one embodiment of the invention, identification of presence of undesirable noise in step 2) may be followed by a signal-processing step during which the cardiac cycles identified as being noisy in step 2) are ignored; and then by the initial analysis step again.

Thus, presence of undesirable noise in the collected signals does not necessarily make the signals unusable.

In one embodiment of the invention, step 3) may further comprise determining a criterion of majority that is determined on the basis of the criterion of similarity by determining the number of cycles that are similar between the collected signals and reference signals representative of a normal sinus cycle. In addition, in an implementation of the invention, the criterion of majority is compared with a predetermined majority threshold that is representative of presence of a tachyarrhythmia episode, thereby making it possible to confirm presence or absence of a tachyarrhythmia episode.

Thus, using the criterion of majority and the defined value for the majority threshold, confirmation of presence of a tachyarrhythmia episode can be deduced. Conversely, it might concluded that oversensing of the T wave and/or of the P wave has taken place, and that therefore no particular treatment is required. The method of processing signals thus makes it possible to distinguish oversensing of T or P waves (or of noise) from tachyarrhythmia; which is necessary in the particular situation of subcutaneous defibrillators, which are more liable to oversense noise and/or P or T waves than transvenous defibrillators are.

BRIEF DESCRIPTION OF THE DRAWINGS

The invention and its advantages are explained in more detail below by means of preferred embodiments and implementations that are described in particular with reference to the following accompanying figures, in which.

DETAILED DESCRIPTION

The invention is described in more detail below by using advantageous embodiments and implementations by way of example and with reference to the figures. The embodiments and implementations described are merely possible configurations, and it should be borne in mind that the individual characteristics as described above may be provided independently from one another or be omitted entirely when implementing the present invention.

Figure 1:
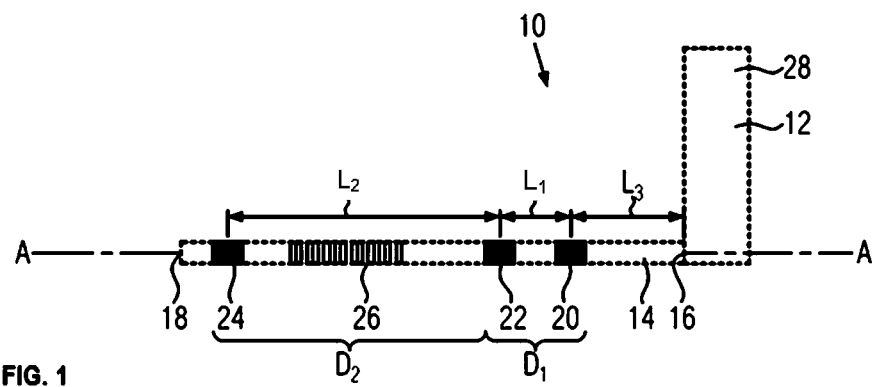
FIG. 1 is a diagrammatic view of a subcutaneous implantable device of the present invention.
Figure 2:
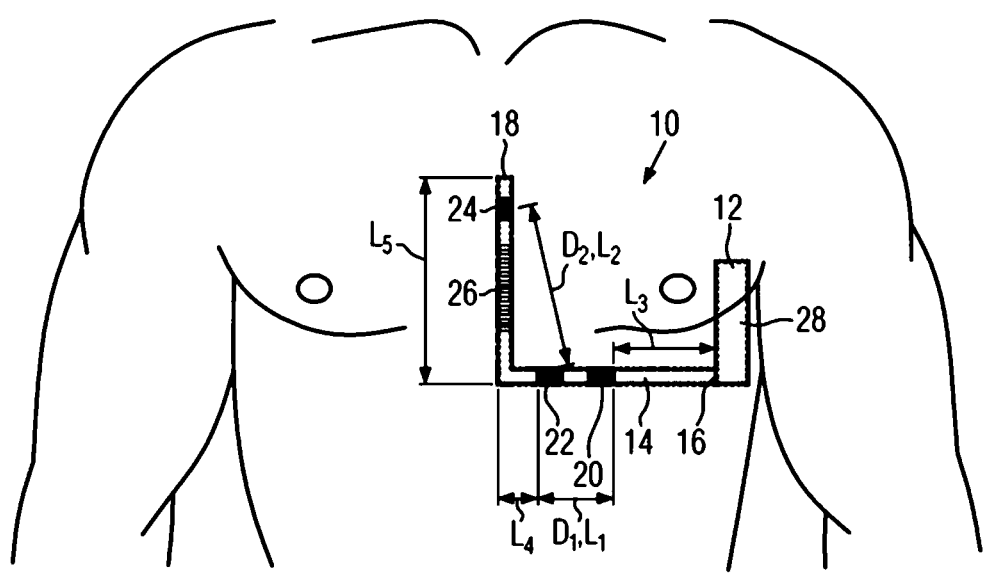
FIG. 2 is a diagrammatic view seen by transparency showing the subcutaneous implantable device of the present invention as implanted in a patient.

FIG. 1 shows a subcutaneous implantable medical device 10, of the subcutaneous defibrillator type 10. FIG. 2 shows said subcutaneous implantable device 10 in an implanted state.

The subcutaneous defibrillator 10 comprises a housing 12, which generates pulses, and to which a subcutaneous implantable lead 14 is connected.

The subcutaneous implantable lead 14 is at least partially flexible and has two ends 16 and 18: a proximal end 16 that is connected to the housing 12 and a free distal end 18.

Figure 3:
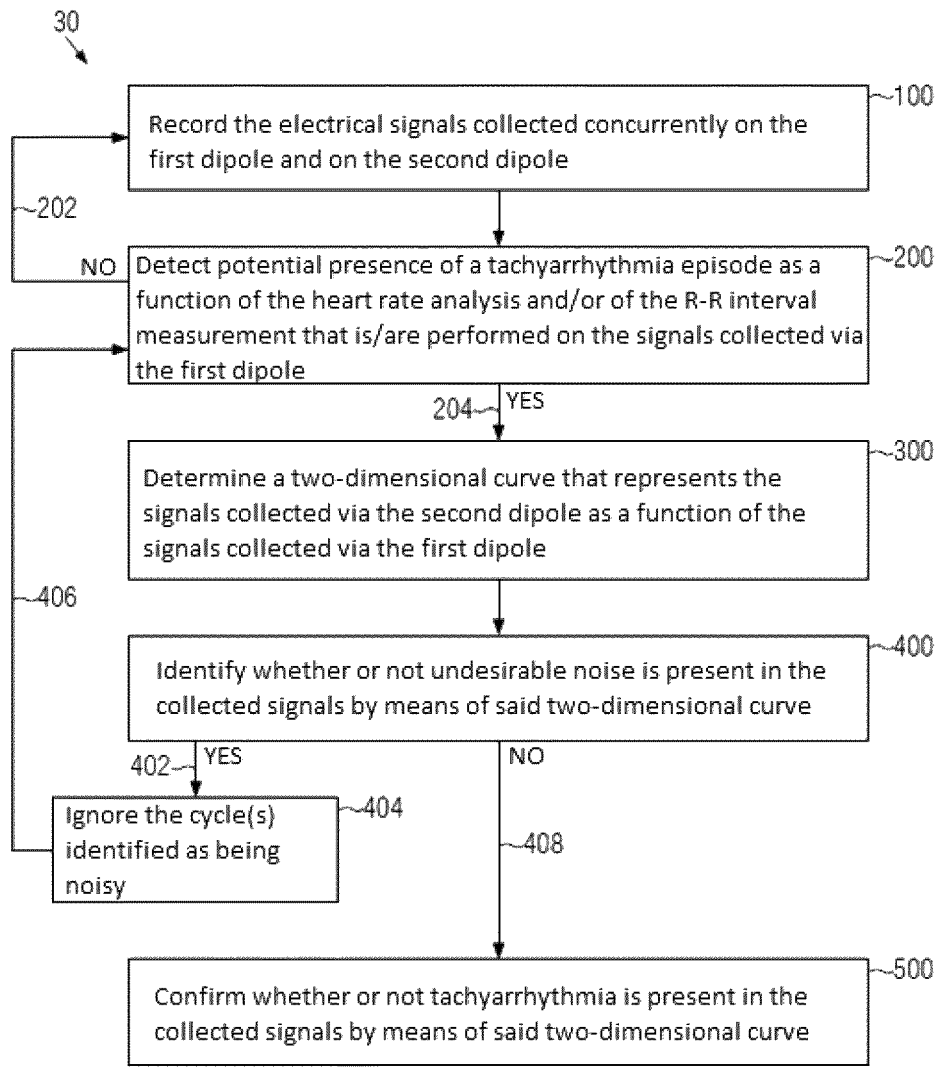
FIG. 3 is a flow chart of the method of the present invention for processing signals.

In the embodiment and the implementation shown in FIGS. 2 and 3, the subcutaneous implantable lead 14 comprises three detection or "sensing" electrodes 20, 22, 24 and one defibrillation electrode 26. In a variant, the subcutaneous implantable lead 14 could comprise more than three sensing electrodes.

The subcutaneous implantable lead 14 also comprise conductor wires (which are not shown), making it possible to connect the electrodes 20, 22, 24 of the lead 14 electrically to electrical contacts (not shown) at the housing 12, which is known per se from the current state of the art.

The sensing electrodes 20, 22, 24 of the subcutaneous implantable lead 14 make it possible to detect electrical signals that are used for deducing the cardiac activity of a patient.

Detecting or sensing electrophysiological activity subcutaneously is, however, degraded by numerous artifacts such as muscle electrical noise or interference with the outside environment. In addition, since the lead 14 is of the subcutaneous type, the sensing electrodes 20, 22, 24 are not in direct contact with the myocardium, i.e. with the cardiac muscle. Appropriate positioning of the detection electrodes 20, 22, 24 makes it possible to improve the quality of the electrophysiological signals detected and collected, thereby making it possible to improve accordingly the quality of detection of the R wave (i.e. of the depolarization peak). In addition, optimum processing of the collected signals makes it possible to further improve in the quality of detection of the R wave.

In order to improve detection of the R wave and in order to minimize detection of P and T cardiac waves, in particular so as to facilitate measuring the R-R interval, the subcutaneous implantable device 10 has specific positioning of the sensing electrodes 20, 22, 24. Specifically, as shown in FIGS. 2 and 3, a first sensing electrode 20 and a second sensing electrode 22 are positioned between the housing 12 and the defibrillation electrode 26, while a third sensing electrode 24 is placed between the distal end 18 of the lead 14 and the defibrillation electrode 26. The defibrillation electrode 26 is thus positioned between the second sensing electrode 22 and the third sensing electrode 24. Thus, in a direction going from the proximal end 16 of the lead 14 to the distal end 18 of the lead 14, the lead comprises, in the following order: the first sensing electrode 20; the second sensing electrode 22, the defibrillation electrode 26, and then the third sensing electrode 24.

The specific positioning of the sensing electrodes 20, 22, 24 is described in terms of length with reference to FIG. 1 only, FIG. 1 showing the lead 14 in a non-implanted state, in which it is not curved and it is aligned along an axis A.

The first sensing electrode 20 and the second sensing electrode 22 form a first dipole $D_1$ of length $L_1$.

In the embodiment shown in FIGS. 1 and 2, the second sensing electrode 22 and the third sensing electrode 24 form a second dipole $D_2$ of length $L_2$. In a variant, the second dipole $D_2$ may be formed by the third sensing electrode 24 and by the first sensing electrode 20. In another variant, the housing 12 may serve as an electrode and form a dipole with one of the sensing electrodes 20, 22, 24.

The length $L_1$ of the first dipole $D_1$ is shorter than the length $L_2$ of the second dipole $D_2$. In particular, the length $L_1$ lies in the range 5 millimeters (mm) to 50 mm, and more particularly in the range 10 mm to 20 mm, while the length $L_2$ lies in the range 80 mm to 400 mm. Furthermore, the distance $L_3$ between the first sensing electrode 20 and the housing 12 lies in the range 80 mm to 300 mm.

The subcutaneous implantable medical device 10 further comprises a controller 28 housed in the housing 12. The controller 28 of the device 10 is configured to detect electrophysiological signals recorded simultaneously via the first dipole $D_1$ and via the second dipole $D_2$ of the subcutaneous implantable lead 14. The controller 28 is configured to detect the R wave of a cardiac signal at the first dipole $D_1$.

Since the first dipole $D_1$ is shorter than the second dipole $D_2$, the first dipole $D_1$ is less exposed to the risk of over-sensing, i.e. of over-detection, in particular because it is less liable to record noise of muscular origin. In addition, while the device 10 is being implanted subcutaneously, the first dipole $D_1$ is positioned close to and above the left lung cardiac notch. This particular positioning of the first dipole $D_1$ makes it possible to detect an electrophysiological signal with an R wave that is more distinctive relative to the P and T waves; the P and T waves detected at this place being minimized relative to the R wave.

In another embodiment, the subcutaneous implantable active medical device 10 may comprise an accelerometer and/or a gyroscope in such a manner that the controller 28 is configured to determine the position of the patient by means of the accelerometer and/or of the gyroscope.

In another embodiment, detection of the R-wave via the first dipole could be combined with detection of cardiac signals on a plurality of "second dipoles", i.e. on a plurality of dipoles that are longer than the first dipole, e.g.: a dipole formed by the second sensing electrode 22 and by the third sensing electrode 24; a dipole formed by the first sensing electrode 20 and by the third sensing electrode 24; and a dipole formed between the housing 12 and one of the sensing electrodes 20, 22, 24.

The electrical signals collected via the first dipole $D_1$ and via the second dipole $D_2$ serve as input signals for an algorithm for processing the signals with the aim of detecting the presence of any tachyarrhythmia. Prior to the processing, it is possible for the signals to undergo appropriate filtering, normalization, and/or centering pre-processing using known techniques.

This method of processing signals is described below generally with reference to FIG. 3, and then in more detail with reference to FIGS. 4a and 4b.

The method 30 of processing signals may be applied to the subcutaneous implantable medical device 10 described above with reference to FIGS. 1 and 2.

The method 30 shown in FIG. 3 comprises a first step 100 during which the signals that are collected in a time domain concurrently via the first dipole $D_1$ and via the second dipole $D_2$ are recorded. Said signals may be recorded over a predetermined time window centered on the detected R wave. In a variant, the signals may be recorded continuously, in particular during a period of suspected tachyarrhythmia. The controller 28 of the device 10 may itself comprise a memory in which said collected signals are stored.

During a second step 200 of the method 30, potential presence of a tachyarrhythmia episode is detected as a function of the signals collected via the first dipole $D_1$ only. This second step 200 may be based on an analysis of the heart rhythm or of the heart rate. In a variant, the step 200 may comprise a morphological analysis. If the presence of a tachyarrhythmia episode is not suspected (see arrow 202 in FIG. 3), the method 30 loops back to the first step 100. Conversely, if the presence of a tachyarrhythmia episode is suspected (see arrow 204 in FIG. 3), the method 30 of processing signals proceeds to a third step 300. Thus, the following steps of the method 30 of processing signals are not performed unnecessarily if the presence of a tachyarrhythmia episode is not even suspected. This makes it possible, in particular, to reduce the costs in terms of software resources and power.

In the third step 300, a two-dimensional curve that is parameterized as a function of time and that is representative of the cardiac activity of a patient is determined by plotting the signals collected via the second dipole as a function of the signals collected via the first dipole. In addition, a tangent vector at a plurality of points of said two-dimensional curve is determined. Said vector may be a normalized vector.

The third step 300 is followed by a fourth step 400 during which presence or absence of undesirable noise in the collected signals is identified on the basis of the change of sign of at least one of the coordinates of the tangent vector between each pair of successive points of the plurality of points of said two-dimensional curve. This method of detecting the presence of undesirable noise makes it possible to reduce the computing costs firstly due to the small number of steps it has, and secondly due to the fact that it does not require any analysis of the amplitude of the collected signals.

If presence of undesirable noise is detected (see arrow 402 in FIG. 3), the fourth step 400 is followed by a step 404 in which the component(s) of any undesirable noise that is detected in the collected signals in step 400 is/are ignored. Step 404 is then followed by the second step 200 (see arrow 406 in FIG. 3), as described above. Conversely, if presence of undesirable noise in the signals is not detected (see arrow 408 in FIG. 3), the method 30 of processing signals proceeds to a fifth step 500.

In the fifth step 500, presence or absence of a tachyarrhythmia episode is confirmed on the basis of a criterion of majority that is determined according to a criterion of similarity between said two-dimensional curve and a reference two-dimensional curve that is representative of a normal sinus cycle, which criterion of majority is described in more detail below.

The method 30 of processing signals and its steps 100 to 500 are described in more detail below with reference to the flow chart of FIGS. 4a and 4b. The reference numerals that share the same hundreds digit refer to the same step, in particular to any one of the steps 100 to 500 that are described above with reference to FIG. 3 and to which reference is made below.

The first step 100, in which the signals collected in a time domain concurrently via the first dipole $D_1$ and via the second dipole $D_2$ are recorded, is followed by a step 102, during which, after each detection of a depolarization peak, i.e. after each detection of an R wave, a corresponding beat is isolated by a time window that is of fixed width and that is centered on said depolarization peak. For example, the time window may have a width of in the range 80 ms to 150 ms that is centered on the detection of the peak of the R wave, in particular a width of 100 ms, corresponding to 100 points for a sampling frequency of 1000 hertz (Hz). This value of 100 milliseconds makes it possible to isolate the QRS complex so as to analyze its morphology. The controller 28 of the device 10 is configured to keep a plurality of successive detected cycles in its memory. Detection of the R wave makes it possible, in particular, to determine the R-R interval.

In an advantageous embodiment of the present invention, detection of the R wave is performed on the basis of the signals collected via the first dipole $D_1$ only. Detection of the R wave is thus not performed on the second dipole $D_2$ so as not to add any computing cost. In addition, since the first dipole $D_1$ is shorter than the second dipole $D_2$, the first dipole $D_1$ is less liable to be degraded, in particular because it is less liable to record noise of muscular origin. Indeed, the geometry of the first dipole $D_1$ of length $L_1$=5 mm to 50 mm, in particular $L_1$=10 mm to 20 mm, enables the first dipole $D_1$ to be rendered less liable to myopotentials. In addition, when the lead is implanted, the position of the dipole $D_1$ makes it possible to optimize detection of the R wave to P wave ratio and of the R wave to T wave ratio, and thus to reduce the risk of oversensing. The signals of the second dipole $D_2$ that are collected concurrently with the signals of the first dipole $D_1$ are, however, kept in the memory and used in step 300 of the method 30 of processing signals.

During the second step 200 of the method 30, potential presence of a tachyarrhythmia episode, which potential presence is based on the R-R intervals of the signals collected via the shorter dipole $D_1$, is determined: if the R-R interval, as computed in the preceding step 102, is less than a predetermined tachyarrhythmia threshold, presence of a tachyarrhythmia episode is suspected. In a variant, potential presence of a tachyarrhythmia episode may be established by considering a moving average over a plurality of cycles, e.g. over from 5 cycles to 20 cycles, and in particular over 8 cycles. The predetermined tachyarrhythmia threshold may have a fixed value or an adjustable value, in particular a value that is programmable for each patient.

As explained with reference to FIG. 3, if the presence of a tachyarrhythmia episode is not suspected (see arrow 202 in FIG. 4a), the method 30 loops back to the first step 100. Conversely, if the presence of a tachyarrhythmia episode is suspected (see arrow 204 in FIG. 4a), the method 30 of processing signals proceeds to the third step 300.

Figure 5:
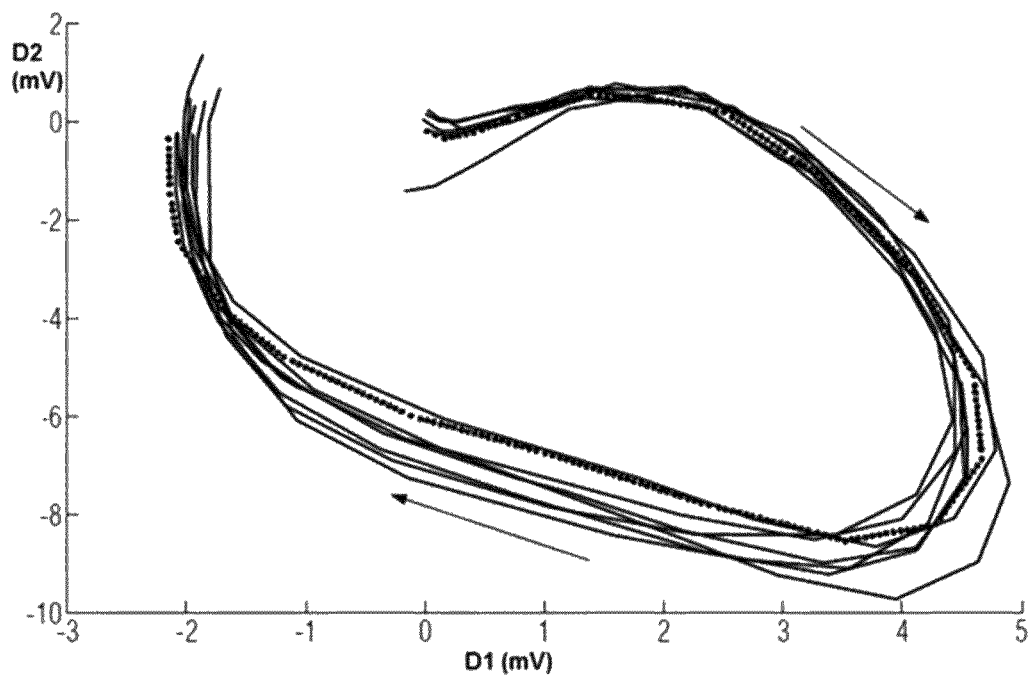
FIG. 5 shows a two-dimensional curve of a non-noisy cycle.

In the third step 300, the successive beats recorded simultaneously and subcutaneously via the first dipole $D_1$ and via the second dipole $D_2$, a fraction of which beats lies within the time window comprising the QRS complex and centered on the R wave, are represented in the form of a two-dimensional curve with the first dipole $D_1$ along the abscissae and the second dipole $D_2$ up the ordinates. In a variant, the second dipole $D_2$ could be along the abscissae and the first dipole $D_1$ up the ordinates. Such a two-dimensional curve is shown in FIG. 5. As shown in FIG. 5, the two-dimensional curve is not a closed loop since it corresponds to only a portion of the full cardiac loop, i.e. to the QRS complex isolated within the time window.

Two-dimensional analysis of the collected signals, i.e. analysis in two dimensions, should not be construed in a manner that is limiting per se, the invention applying equally well to analysis in a multi-dimensional space of higher order (three-dimensional or higher), by extrapolating the teaching of the present description to a situation in which signals are collected subcutaneously and concurrently via three or more dipoles.

Figure 4A:
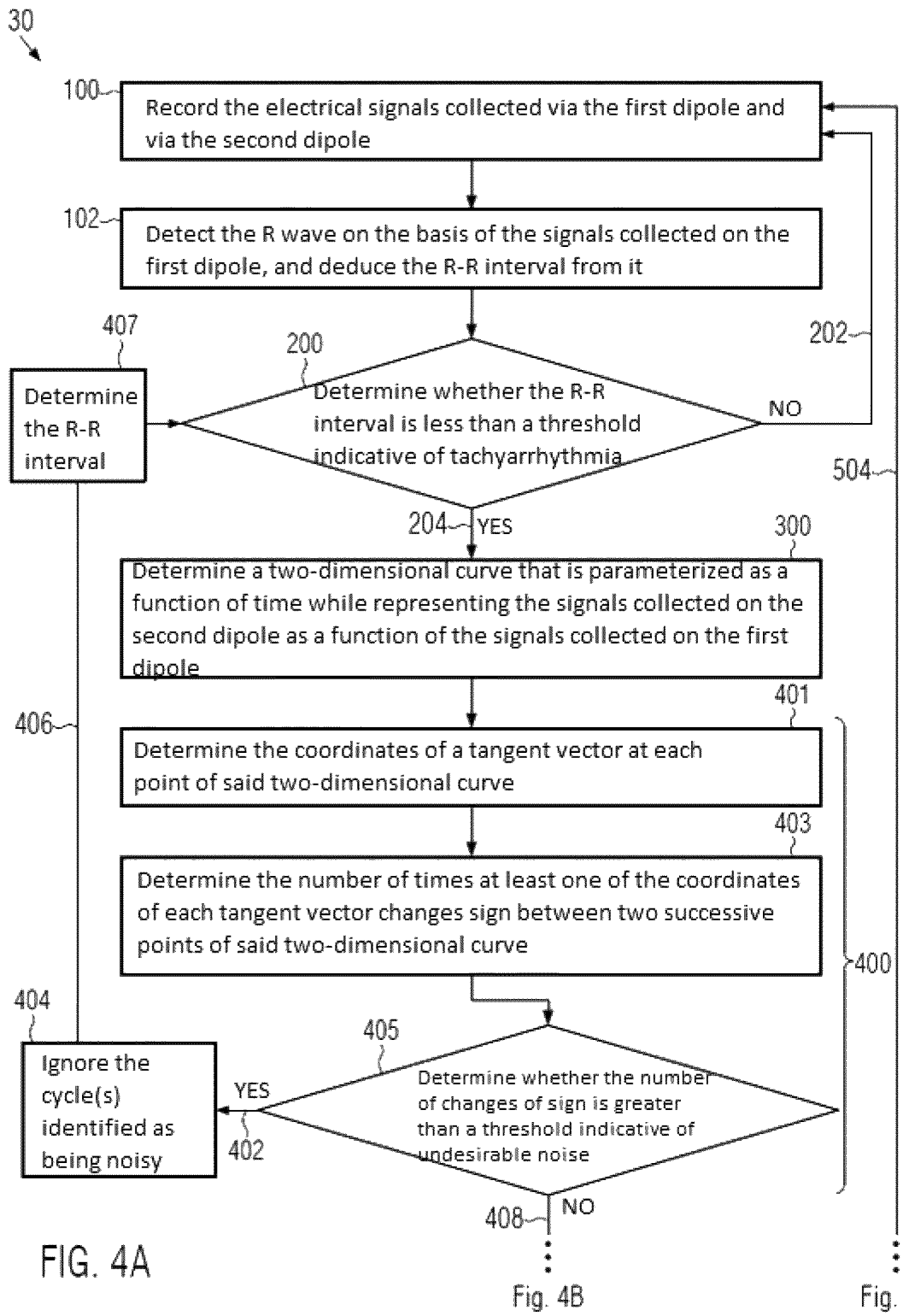
FIG. 4*a* is a detailed flow chart of the method shown in FIG. 3 for processing signals.

As shown in FIG. 4a, the step 400 of the method 30, in which step the presence or absence of undesirable noise in the collected signals is identified, comprises three successive sub-steps 401, 403, and 405.

In the first sub-step 401 of step 400, the coordinates of a tangent vector at each point of the two-dimensional curve determined in step 300 are computed.

In the second sub-step 403 of the step 400, the algorithm of the method 30 computes the number of times that at least one of the two coordinates of each tangent vector changes sign between two successive points on the two-dimensional curve.

Figure 6:
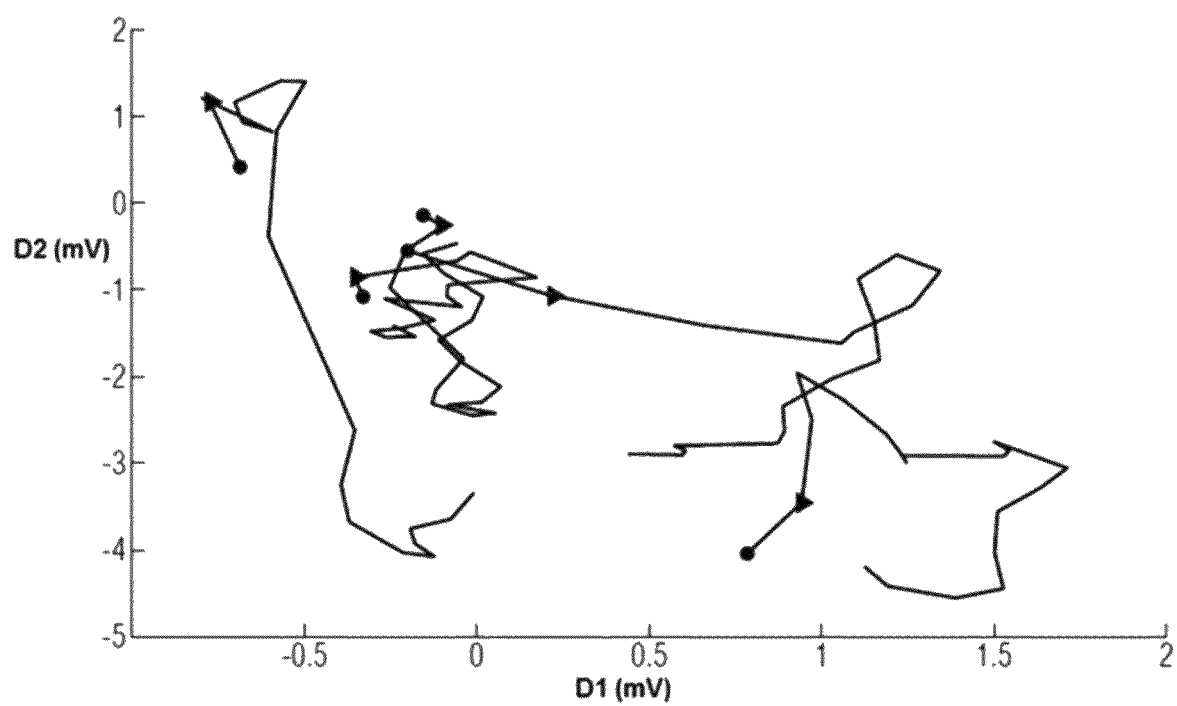
FIG. 6 shows a two-dimensional curve of a noisy cycle.

The second sub-step 403 thus makes it possible to characterize the curvature of the two-dimensional curve. Indeed, for a non-noisy cardiac cycle, a relationship exists between the signals collected via the two dipoles $D_1$ and $D_2$ that means that the two-dimensional curve is represented in essentially uniform manner. Conversely, for a noisy cardiac cycle, i.e. for a cycle comprising artifacts of extracardiac origin, the two-dimensional curve can be represented erratically, as shown in FIG. 6. Such an erratic representation (see FIG. 6) is then characterized, in accordance with the present invention, by the number of times that at least one of the coordinates of the tangent vector changes sign between each pair of successive points of the two-dimensional curve.

In the third sub-step 405 of step 400, the algorithm of the method 30 compares said number of changes of sign with a predetermined threshold number that is indicative of undesirable noise. The predetermined threshold number indicative of undesirable noise may be defined relative to all of the plurality of points of said two-dimensional curve. In a variant, this predetermined threshold number that is indicative of undesirable noise may be defined as being an absolute threshold for a certain number of given consecutive points.

If presence of undesirable noise in the signals is not detected (see arrow 408 in FIGS. 4a and 4b), the method 30 of processing signals proceeds to the fifth step 500.

Conversely, if presence of undesirable noise is detected in the signals (see arrow 402 in FIG. 4a), the sub-step 405 of step 400 is followed by a step 404 in which the component(s) of undesirable noise in the collected signals that is detected in step 400 is/are ignored. In a variant, after a certain given number of detected noisy cycles, the algorithm triggers a mode referred to as "noise mode", in which parameters, in particular the threshold for detecting the R waves, are temporarily modified for a certain lapse of time, e.g. for 30 seconds. In another variant, the algorithm, in noise mode, lengthens the refractory periods for a certain predefined lapse of time.

Step 404 is followed by a step 407 (see arrow 406 in FIG. 4a) during which the R-R interval is computed again on the signals in which the undesirable noise has been ignored and therefore not taken into account. Step 407 is then followed by above-described step 200, during which the R-R interval of the signals, from which the undesirable noise has been cleaned, is compared with a threshold indicative of tachyarrhythmia.

Figure 4B:
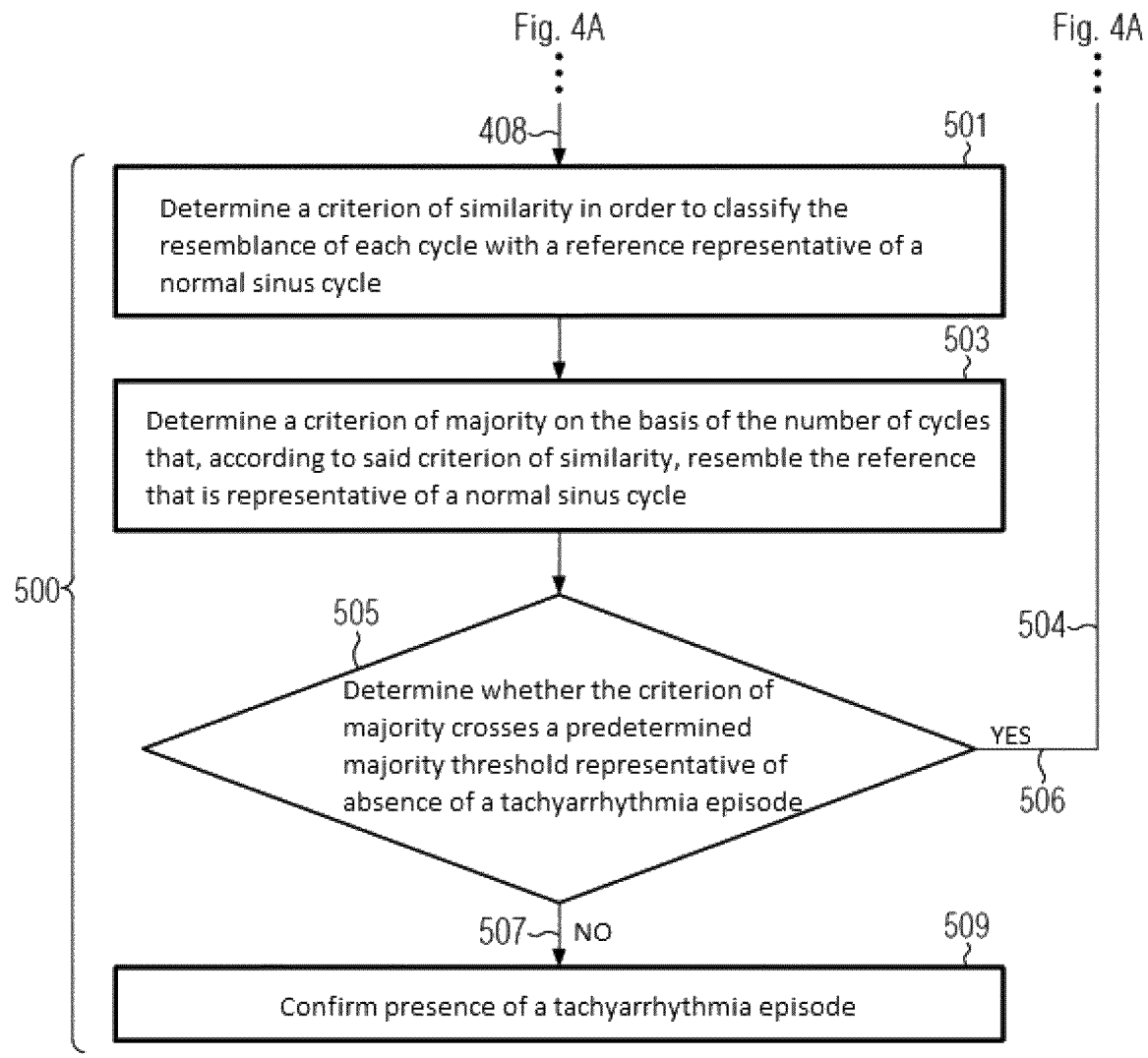
FIG. 4*b* is a detailed flow chart of the method shown in FIG. 3 for processing signals.

As shown in FIG. 4b, step 500 of the method 30, in which the presence or absence of tachyarrhythmia is confirmed, comprises three successive sub-steps 501, 503, 505, and 509.

In the first sub-step 501 of step 500, in which the signals do not contain undesirable noise but in which the R-R interval is less than the threshold indicative of tachyarrhythmia (see step 200 of the method 30), a comparison analysis, in particular a similarity analysis, is begun. Thus, in sub-step 501, the two-dimensional curve determined in step 300 is compared with a reference two-dimensional curve that is representative of a normal sinus rhythm, and that is, for example, pre-recorded in the memory of the controller 28.

In a variant, step 501 may comprise determining a criterion of similarity by considering, in addition to a normal sinus cycle, a reference representative of a "P wave" and a reference representative of a "T wave". Thus, step 501 of this variant makes it possible to identify potential P/T oversensing because, at the same time, there would be a "similarity to the T reference" or a "similarity to the P reference".

In order to classify the resemblance of each cycle with the reference representative of a normal sinus rhythm, a criterion of similarity is determined in step 501. Using the criterion of similarity, each cycle is classified either as "resembles the normal sinus rhythm" or as "does not resemble the normal sinus rhythm".

Figure 7:
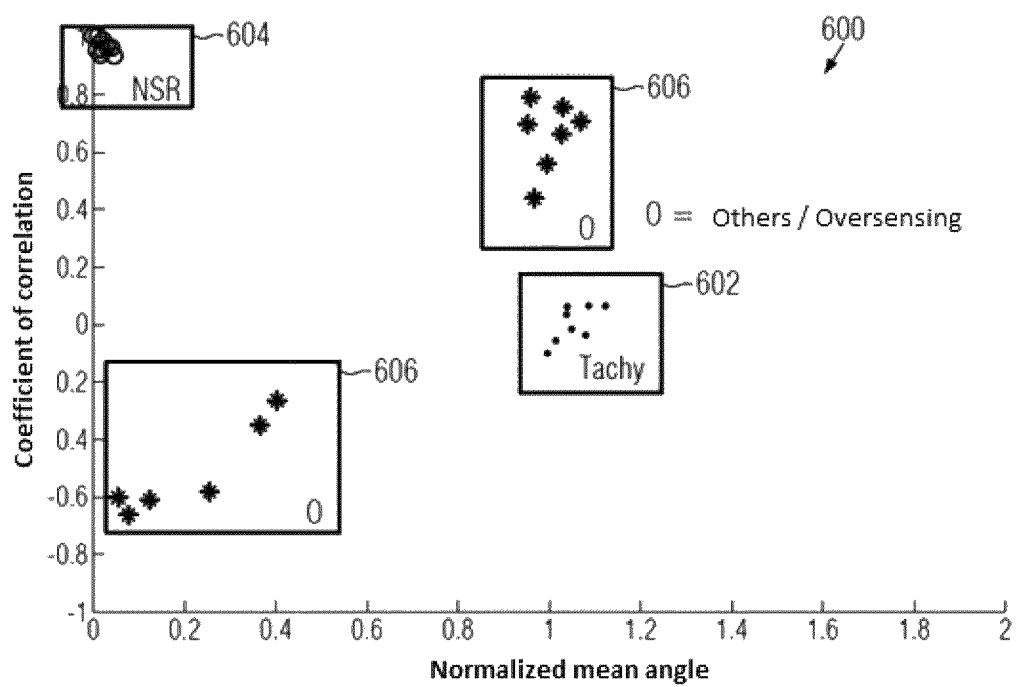
FIG. 7 shows a distribution defined for discriminating the presence of tachyarrhythmia.

In order to determine the criterion of similarity, tangent vectors of each curve at each point are determined. Then, a mean angle between the tangent vectors of the two curves at each point is determined. Then, a coefficient of correlation between the norms of the tangent vectors of the two curves at each point is determined. Finally, the mean angle and the coefficient of similarity are represented on a graph, as shown in FIG. 7, from which it is possible to determine whether or not the curves are mutually similar. The graph in FIG. 7 represents the classification of each cycle as "similar" to the sinus reference or "not similar" to the sinus reference. In the event of classification as "not similar", it is not possible, at this stage of the method 30, to know whether the cycle is representative of oversensing or of tachyarrhythmia. That is why, at a sub-step 503 of step 500, a criterion of majority is determined.

The criterion of majority may be a function, over the last N non-noisy beats recorded, of the number of cycles $C_i$ similar to those of the reference that is representative of a normal sinus rhythm (NSR). In a variant, the criterion of similarity may also be defined by a ratio $C_i$ to N ($C_i/N$) where N is the number of last non-noisy beats recorded. The similarity of the cycles with the cycles of the reference is thus determined by means of the criterion of similarity in step 501.

In a sub-step 505 of step 500, this criterion of majority, i.e. the value of $C_i$ or the ratio $C_i/N$, is compared with a predetermined majority threshold representative of absence of a tachyarrhythmia episode $C_{ref}$.

If a majority of cycles similar to the sinus reference (e.g. 8 $C_i$ out of the last 12 cycles) is detected, then presence of tachyarrhythmia is not confirmed. The method 30 is then reinitialized so that step 505 is followed by the first step 100 of the algorithm (see arrow 506 in FIG. 4*b*), i.e. the step of acquiring new electrical signals.

Conversely, if a majority of cycles similar to the sinus reference (e.g. 2 $C_i$ out of the last 12 cycles) is detected, then tachyarrhythmia is confirmed in step 509.

Thus, depending on whether or not the criterion of majority crosses a predetermined threshold $C_{ref}$, the algorithm concludes that a tachyarrhythmia episode is present or absent.

Figure 8:
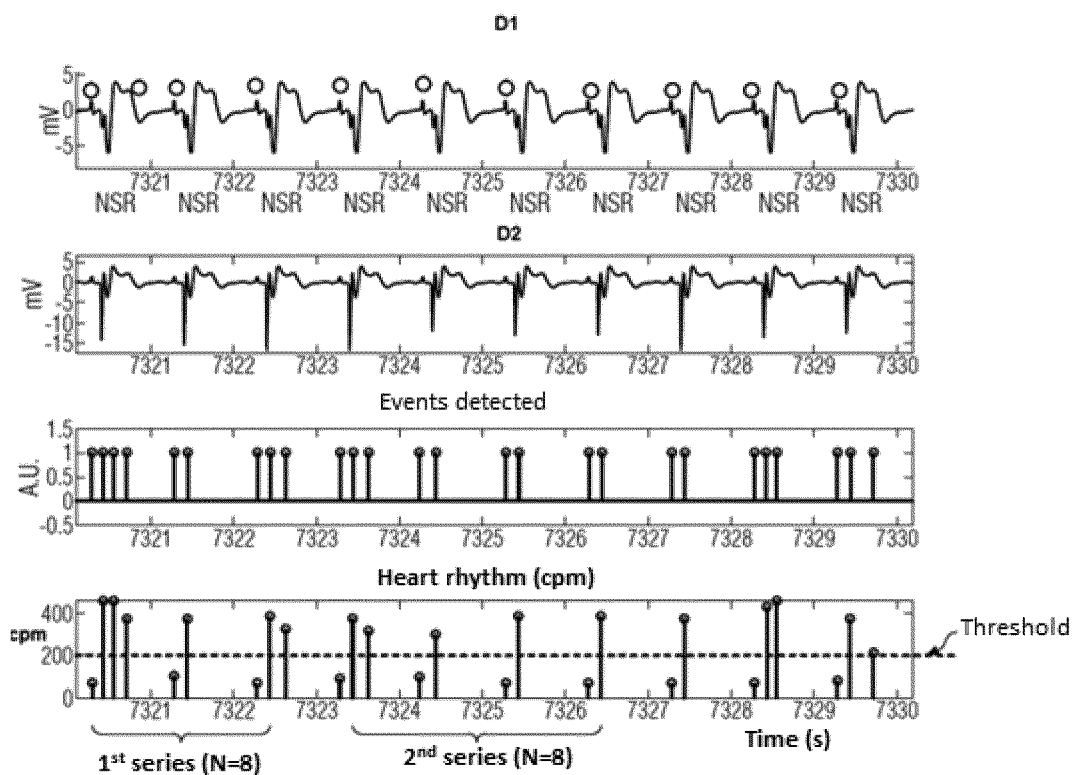
FIG. 8 shows a signal classified by the method of the present invention as being a normal sinus rhythm.

FIG. 8 shows an example in which the first series of 8 beats (N=8) comprises 3 cycles that resemble the cycle representative of a normal sinus rhythm ($C_i$=3). The 5 cycles that do not resemble the cycle representative of a normal sinus rhythm are indicated by symbols "o". Thus, in the example shown in FIG. 7, the criterion of majority of the first series is equivalent to a ratio of 3/8.

In the second series of 8 beats shown in FIG. 8, the criterion of majority is equivalent to a ratio of 4/8.

When $C_{ref}$ is predetermined as being a value greater than or equal to 3/8, then the algorithm does not confirm presence of a tachyarrhythmia episode following the analysis of the first series of beats and of the second series of beats of FIG. 8.

Figure 9:
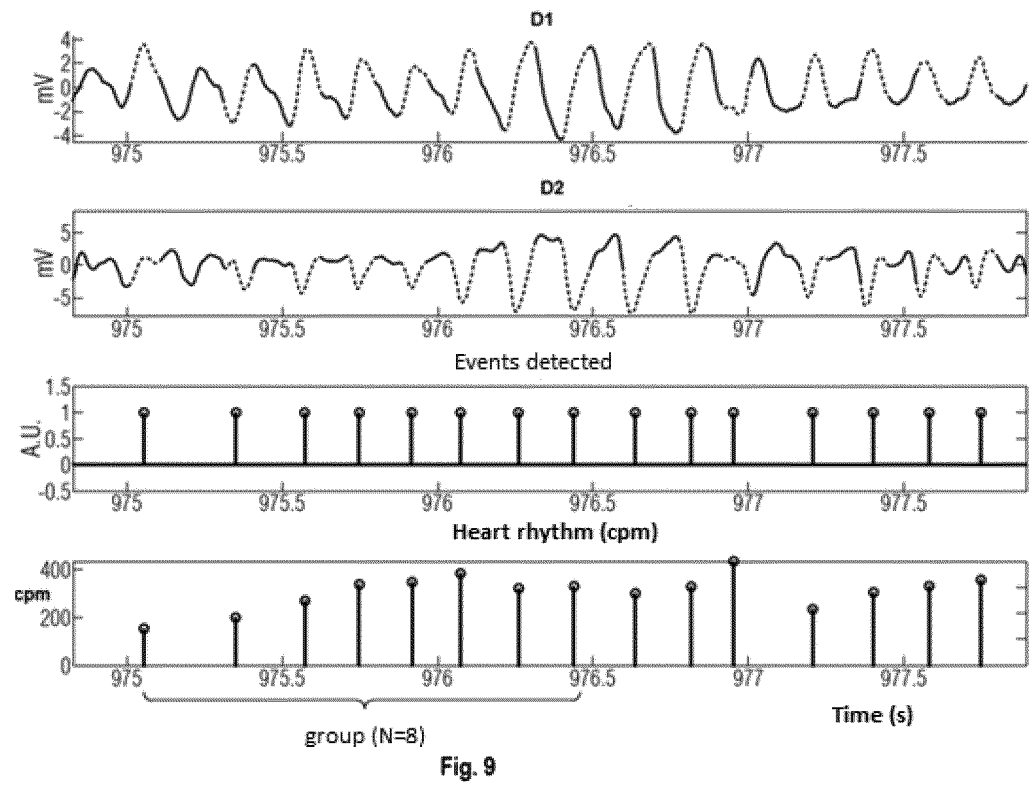
FIG. 9 shows a signal classified by the method of the present invention as being a tachycardia event.

FIG. 9 shows an example in which no cycle resembles the cycle representative of a normal sinus rhythm. Thus, in the example shown in FIG. 8, N=8 and $C_i$=0. The criterion of majority of the example shown in FIG. 9 is thus zero, and thus necessarily less than the threshold $C_{ref}$. In such a situation, the presence of a tachyarrhythmia episode is then confirmed in step 509 and checked over a plurality of moving windows.

The reference two-dimensional curve representative of a normal sinus rhythm is determined by taking the mean and/or the median of at least the last two cycles of normal sinus rhythm of the patient.

In an embodiment in which the subcutaneous implantable medical device 10 comprises an accelerometer and/or a gyroscope, the controller 28 of the device 10 could, in addition, be configured to determine the criterion of similarity by comparing said two-dimensional curve with a reference two-dimensional curve in said predetermined position and representative of a normal sinus rhythm. Thus, by making it possible to detect the position of the patient, interpretation of the collected electrical signals can be made finer, and therefore improved. In addition, the reference two-dimensional curves determined at a normal sinus rhythm for each position may be compared with one another so as to keep in the memory only those that differ sufficiently from one position to another. This makes is possible, in particular, to save storage memory. Furthermore, the reference curves for each position may be updated, e.g. daily or weekly.

After step 509, the controller 28 of the device 10 may be configured to trigger a defibrillation operation by means of the defibrillation electrode 26 of the subcutaneous implantable lead 14.

The controller 28 of the device 10 is configured to perform each of the steps and sub-steps of the method 30.

The embodiments and implementations described are merely possible configurations, and it should be borne in mind that the individual characteristics of the embodiments and implementations may be combined or be provided independently from one another.

The invention claimed is:

1. A subcutaneous implantable active medical device comprising:
   a housing;
   a subcutaneous implantable lead connected to the housing, the subcutaneous implantable lead comprising a plurality of sensing electrodes forming at least two dipoles on the subcutaneous implantable lead including a first dipole and a second dipole, from which at least two electrical signals are collected concurrently; and
   a controller configured to:
      perform an initial analysis that includes determining a two-dimensional curve parameterized as a function of time and representative of cardiac activity of a patient by plotting second electrical signals collected via the second dipole as a function of first electrical signals collected via the first dipole, and determining a tangent vector at a plurality of points of said two-dimensional curve;
      utilize the two-dimensional curve to determine whether the collected signals include undesirable noise including identifying the undesirable noise in the collected signals as a function of a change of sign of at least one of coordinates of the tangent vector between each pair of successive points of the plurality of points of said two-dimensional curve;
      in response to determining that the collected signals include the undesirable noise, perform the initial analysis again to determine an updated two-dimensional curve without the identified undesirable noise;
      utilize the updated two-dimensional curve to confirm a presence of a tachyarrhythmia episode on a basis of a criterion of similarity between said updated two-dimensional curve and a reference two-dimensional curve that is representative of a normal sinus rhythm; and
      subsequent to confirming the presence of the tachyarrhythmia episode, trigger a defibrillation operation.

2. The subcutaneous implantable active medical device of claim 1, wherein the electrical signals collected via the first dipole and via the second dipole of the subcutaneous implantable lead are considered over a time window comprising a QRS complex and centered on detection of an R wave, detection of the R wave being performed via the first dipole only.

3. The subcutaneous implantable active medical device of claim 2, wherein the controller is configured to combine the first electrical signals collected via the first dipole and the second electrical signals collected via the second dipole.

4. The subcutaneous implantable active medical device of claim 1, wherein utilizing the two-dimensional curve to determine whether the collected signals include noise includes determining a number of times at least one of the coordinates of the tangent vector changes sign between each pair of successive points of the plurality of points of said two-dimensional curve and by comparing that number with a predetermined threshold number indicative of undesirable noise.

5. The subcutaneous implantable active medical device of claim 1, wherein the controller is further configured to determine the presence of the tachyarrhythmia episode by determining a criterion of majority that is determined on the basis of a criterion of similarity by computing the number of cycles that are similar between the collected signals and reference signals that are representative of a normal sinus cycle.

6. The subcutaneous implantable active medical device of claim 1, wherein the subcutaneous implantable lead further comprises a defibrillation electrode.

7. The subcutaneous implantable active medical device of claim 1, further comprising an accelerometer and/or a gyroscope in such a manner that the controller is configured to determine a position of the patient by means of the accelerometer and/or of the gyroscope, the controller further being configured to determine the criterion of similarity by comparing said updated two-dimensional curve with the reference two-dimensional curve in said determined position.

8. A method of operating a subcutaneous implantable active medical device, the subcutaneous implantable active medical device including a subcutaneous implantable lead comprising a plurality of sensing electrodes forming at least two dipoles on the subcutaneous implantable lead including a first dipole and a second dipole, the method comprising steps of:
  performing an initial analysis that includes determining a two-dimensional curve parameterized as a function of time and representative of cardiac activity of a patient by plotting second electrical signals collected via the second dipole as a function of first electrical signals collected via the first dipole, and determining a tangent vector at a plurality of points of said two-dimensional curve;
  utilizing the two-dimensional curve to determine whether the collected signals include undesirable noise including identifying the undesirable noise in the collected signals as a function of a change of sign of at least one of coordinates of the tangent vector between each pair of successive points of the plurality of points of said two-dimensional curve;
  determine that the collected signals include the undesirable noise, performing the initial analysis again to determine an updated two-dimensional curve without the identified undesirable noise;
  utilizing the updated two-dimensional curve to confirm a presence a tachyarrhythmia episode on a basis of a criterion of similarity between the updated two-dimensional curve and a reference two-dimensional curve that is representative of a normal sinus rhythm; and
  subsequent to confirming the presence of the tachyarrhythmia episode, triggering a defibrillation operation.

9. The method of claim 8,
  wherein, in the initial analysis step, the signals collected via one of the dipoles of the subcutaneous implantable lead are compared with a predetermined tachyarrhythmia threshold.

10. The method of claim 8, wherein utilizing the two-dimensional curve to determine whether the collected signals include includes determining whether a number of times at least one of the coordinates of the tangent vector changes sign between each pair of successive points of the plurality of points of said two-dimensional curve is greater than a predetermined threshold number indicative of undesirable noise.

11. The method of claim 10, wherein the predetermined threshold number indicative of undesirable noise is defined relative to all of the plurality of points of said two-dimensional curve.

12. The method of claim 8, wherein utilizing the updated two-dimensional curve to confirm a presence a tachyarrhythmia episode includes determining a criterion of majority that is determined on the basis of the criterion of similarity by determining a number of cycles that are similar between the collected signals and reference signals representative of a normal sinus cycle.

13. The method of claim 12, wherein the criterion of majority is compared with a predetermined majority threshold that is representative of presence of a tachyarrhythmia episode, thereby making it possible to confirm the presence of a tachyarrhythmia episode.

14. The subcutaneous implantable active medical device of claim 1, wherein the subcutaneous implantable active medical device is a subcutaneous cardiac defibrillator.

15. The subcutaneous implantable active medical device of claim 1, wherein the first dipole has a first length less than a second length of the second dipole.

* * * * *